US008512366B2

(12) United States Patent
Robbins

(10) Patent No.: US 8,512,366 B2
(45) Date of Patent: Aug. 20, 2013

(54) LANCING DEVICE WITH TETHERED DEPTH-CONTROL MECHANISM

(75) Inventor: Avi M. Robbins, Atlanta, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 144 days.

(21) Appl. No.: 13/082,687

(22) Filed: Apr. 8, 2011

(65) Prior Publication Data

US 2011/0313438 A1 Dec. 22, 2011

Related U.S. Application Data

(60) Provisional application No. 61/322,423, filed on Apr. 9, 2010.

(51) Int. Cl.
*A61B 5/151* (2006.01)
*A61B 17/32* (2006.01)

(52) U.S. Cl.
USPC ........................................................ 606/181

(58) Field of Classification Search
USPC ................. 600/564, 566, 567, 583; 606/167, 606/170, 172, 173, 181–183, 185
See application file for complete search history.

(56) References Cited

U.S. PATENT DOCUMENTS

| 6,022,366 | A | 2/2000 | Schraga |
| 6,156,051 | A | 12/2000 | Schraga |
| 6,322,575 | B1 | 11/2001 | Schraga |
| 6,811,557 | B2 | 11/2004 | Schraga |
| 6,887,253 | B2 | 5/2005 | Schraga |
| 7,105,006 | B2 | 9/2006 | Shraga |
| 7,175,641 | B1 | 2/2007 | Schraga |
| 7,311,718 | B2 | 12/2007 | Schraga |
| 2008/0077167 | A1* | 3/2008 | Flynn et al. .................... 606/172 |
| 2008/0146966 | A1 | 6/2008 | Levaughn et al. |
| 2008/0269639 | A1* | 10/2008 | Korner et al. ................. 600/583 |

FOREIGN PATENT DOCUMENTS

| EP | 1764037 A1 | 3/2007 |
| EP | 1797822 A1 | 6/2007 |
| WO | 2009069720 A1 | 6/2009 |
| WO | 2010080584 A1 | 7/2010 |

OTHER PUBLICATIONS

ISR and Written Opinion of PCT/US2011/031685; Jul. 26, 2011; 14 pgs.

* cited by examiner

*Primary Examiner* — Ryan Severson

(74) *Attorney, Agent, or Firm* — Gardner Groff Greenwalk & Villanueva, PC

(57) ABSTRACT

A lancing device having a housing with a proximal end, a distal end and a longitudinal axis. The lancing device also has a lancet carrier translatably supported with respect to the housing. The lancet carrier has a proximal end and a distal end. The lancing device additionally has a depth-control mechanism with a positioning tab adapted to engage the housing, and a tether secured with respect to the positioning tab and the lancet carrier.

16 Claims, 10 Drawing Sheets

LANCING DEVICE WITH TETHERED DEPTH-CONTROL MECHANISM

CROSS-REFERENCE TO RELATED APPLICATION

This application claims the benefit of U.S. Provisional Patent Application Ser. No. 61/322,423, filed Apr. 9, 2010, the entirety of which is hereby incorporated herein by reference for all purposes.

TECHNICAL FIELD

The present invention relates generally to the field of medical devices, and more particularly to a lancing device for blood sampling and testing.

BACKGROUND

Lancing devices are utilized for penetrating the skin of a human or animal subject at a lancing site to obtain a sample of blood or other body fluid for medical testing, as in blood-typing or blood-glucose testing. Commercially-available lancing devices typically include a housing containing a drive mechanism, a charging mechanism for energizing the spring or other drive means of the drive mechanism, and a release mechanism for releasing the drive mechanism upon actuation.

A lancet is typically propelled by the drive mechanism from a retracted position within the housing to an extended position wherein a sharp tip portion of the lancet projects from the housing to prick the subject's skin at a desired lancing site. The lancet is typically a disposable component that is removably mounted into a receiver or lancet carrier portion of the drive mechanism of a lancing device. A used lancet typically is removed from the lancet carrier after sampling for subsequent disposal. An ejection mechanism can optionally be included for discharge of the used lancet from the lancing device. A new, sterile lancet is then replaced into the lancet carrier for further sampling.

A depth-control mechanism can optionally be provided to adjust the penetration depth of the lancet, to control sample size and/or to minimize pain. Commercially-available depth control mechanisms typically include endcaps that are adjustably positioned relative to the lancing device housing, and movable stops that limit the travel of the drive mechanism by contact with the lancet carrier.

Needs exist for an improved depth control mechanism for use with a lancing device. It is to the provision of improved lancing devices and lancing depth control mechanisms that the present invention is primarily directed.

SUMMARY

The present invention provides an improved lancing device with a depth control mechanism including a tether or linkage for adjustment of the lancet penetration depth. In example embodiments, adjustment of the lancing depth is controlled by varying the point of contact or connection of the tether or linkage to the lancing device housing, and/or by varying the length or degree of extension of the tether or linkage.

In a first aspect, the present invention is a lancing device including a housing having a proximal end, a distal end and a longitudinal axis. The lancing device has a lancet carrier translatably supported with respect to the housing. The lancet carrier has a proximal end and a distal end. And, the lancing device has a depth-control mechanism with a positioning tab adapted to engage the housing, and a tether secured with respect to the positioning tab and the lancet carrier.

In a second aspect, the present invention is a depth-control mechanism for a lancing device having a drive-mechanism-driven lancet carrier translatably secured within a housing. The depth-control mechanism includes an engagement body adapted to releasably engage a predetermined location on the housing. The depth-control mechanism also includes a tether connected between the engagement body and the lancet carrier. The tether is adapted to transition between a retracted state and an extended state. And, the depth-control mechanism is adapted to control the distance the lancet carrier is driven with respect to the housing.

In a further aspect, the present invention is a depth-control mechanism for a lancing device with a drive-mechanism-driven lancet carrier translatably secured within a housing. The depth-control mechanism includes an engagement body adapted to releasably engage a predetermined location on the housing. The depth-control mechanism also includes a joint with a first member pivotally connected with respect to the engagement body and a second member pivotally connected with respect to the lancet carrier. The first member is pivotally connected to the second member. And, the depth-control mechanism is adapted to control the distance the lancet carrier is driven with respect to the housing.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
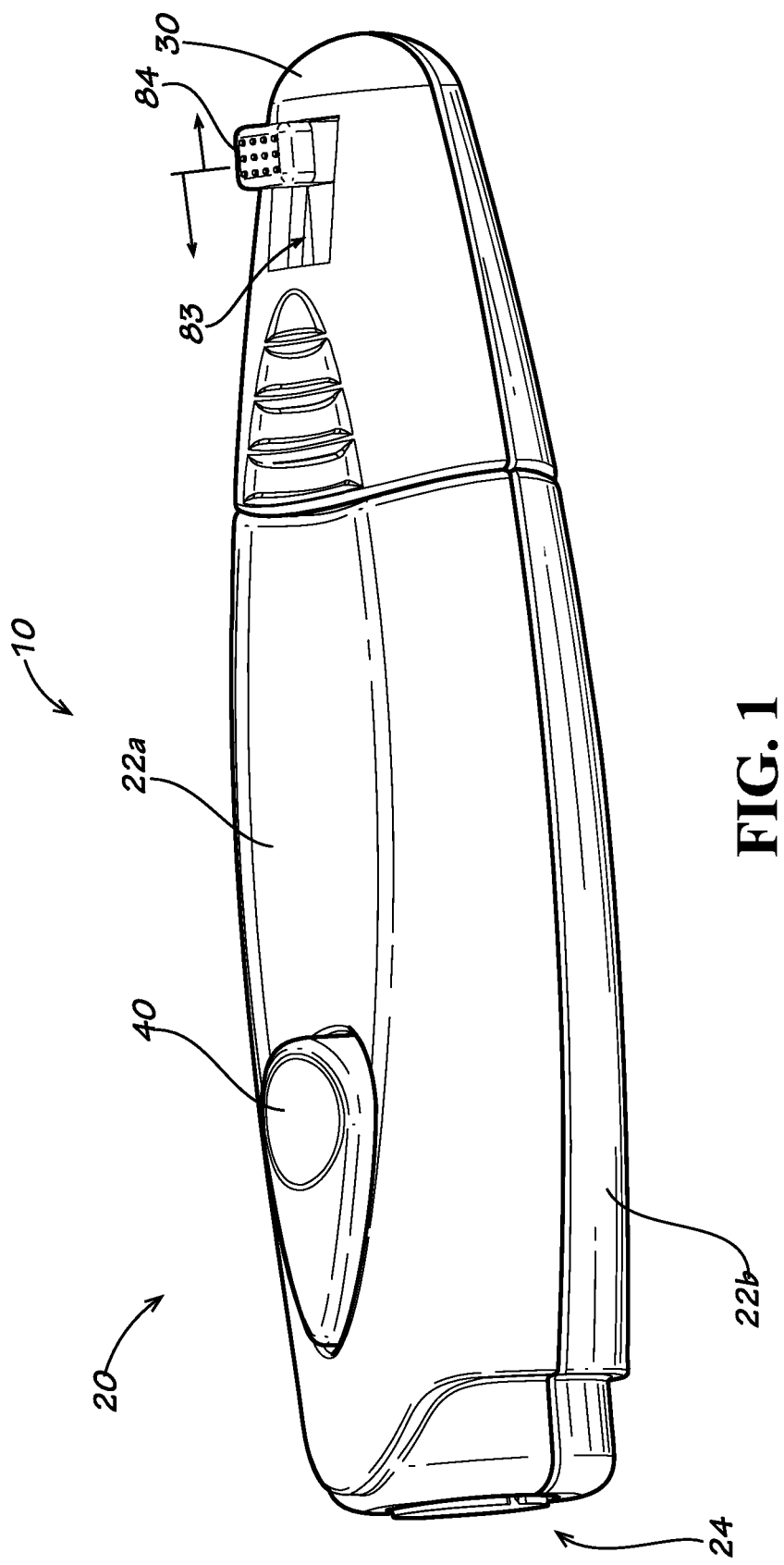
FIG. 1 is a perspective view of a lancing device according to an example embodiment of the present invention.

With reference now to the drawing figures, wherein like reference numbers represent corresponding parts throughout the several views, FIG. 1 shows a lancing device 10 according to an example embodiment of the invention. The device 10, as depicted, includes a housing 20 generally comprising separable upper and lower housing shells 22a, 22b, and a forward or proximal end 24 defining a lancet opening through which at least a sharp tip portion of a lancet projects at the extended position of a lancing stroke to penetrate the skin of a subject during the lancing process. The housing 20 protects a lancet carrier (shown in FIGS. 2-11) that is secured within the shells 22a, 22b. As depicted, the housing 20 has an elongated ergonomic shape, however, alternate shapes can be effective. The housing 20 can be constructed of a rigid durable material, for example plastic.

A release button 40 projects through an opening in the upper housing shell 22a to release a trigger mechanism (shown in FIGS. 2-11) when depressed, thereby actuating the device to move the lancet from a retracted position within the housing 20 to the extended position wherein at least the sharp tip portion (shown in FIG. 10) of the lancet projects outwardly of the lancet opening at the proximal end of the housing 24.

A charging handle 30 forming the rear or distal end of the housing 20 retracts the lancet carrier and energizes a drive spring (shown in FIGS. 2-11) to provide motive force to propel the lancet along the lancing stroke when the device is actuated. As depicted, the charging handle 30 has separable upper and lower shells, however, alternate structures can be effective. The charging handle 30 has an elongated opening 83 through which a distal positioning tab 84 extends. As depicted, the positioning tab 84 can be moved proximally or distally within the limits of the opening 83. The positioning tab 84 can be pushed downward during distal or proximal movement and then can reflexively return vertically upward to a stabilized position. The charging handle 30 can be constructed of a rigid material, for example plastic. As depicted, the charging handle 30 can be a separable body from the housing 20 or the charging handle can be an integral part of the housing.

Figure 2:
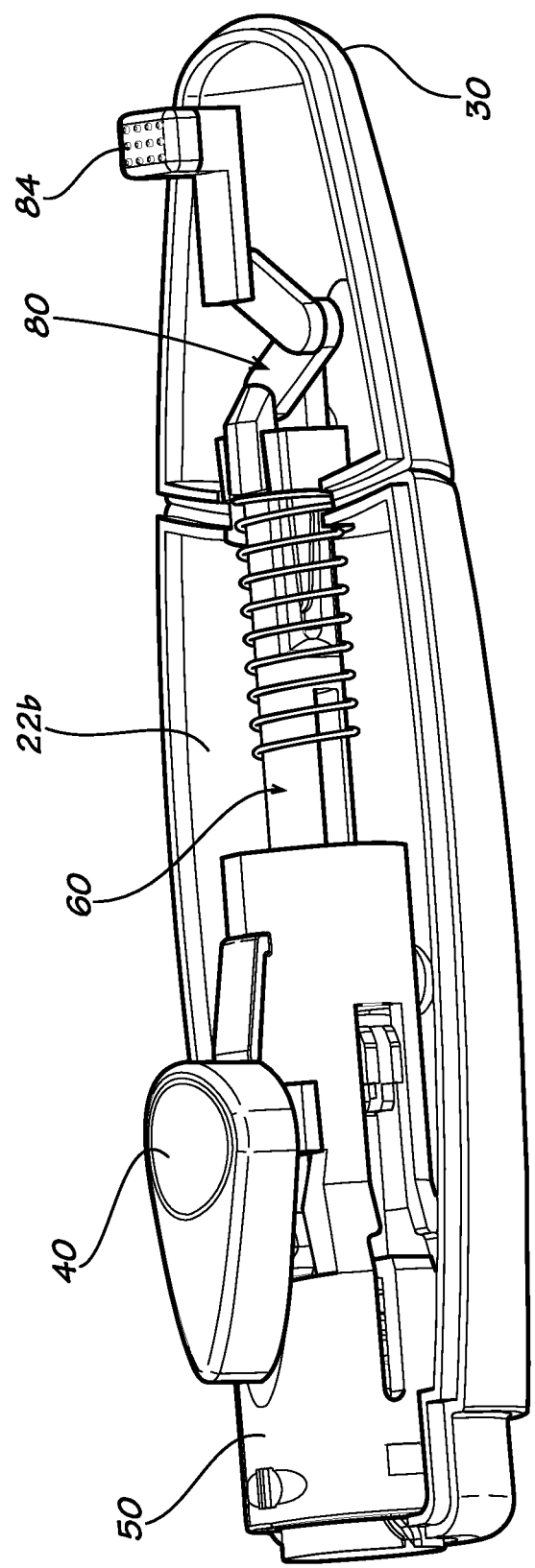
FIG. 2 is the lancing device of FIG. 1 with portions of its external housing removed to show internal components thereof.
Figure 3:
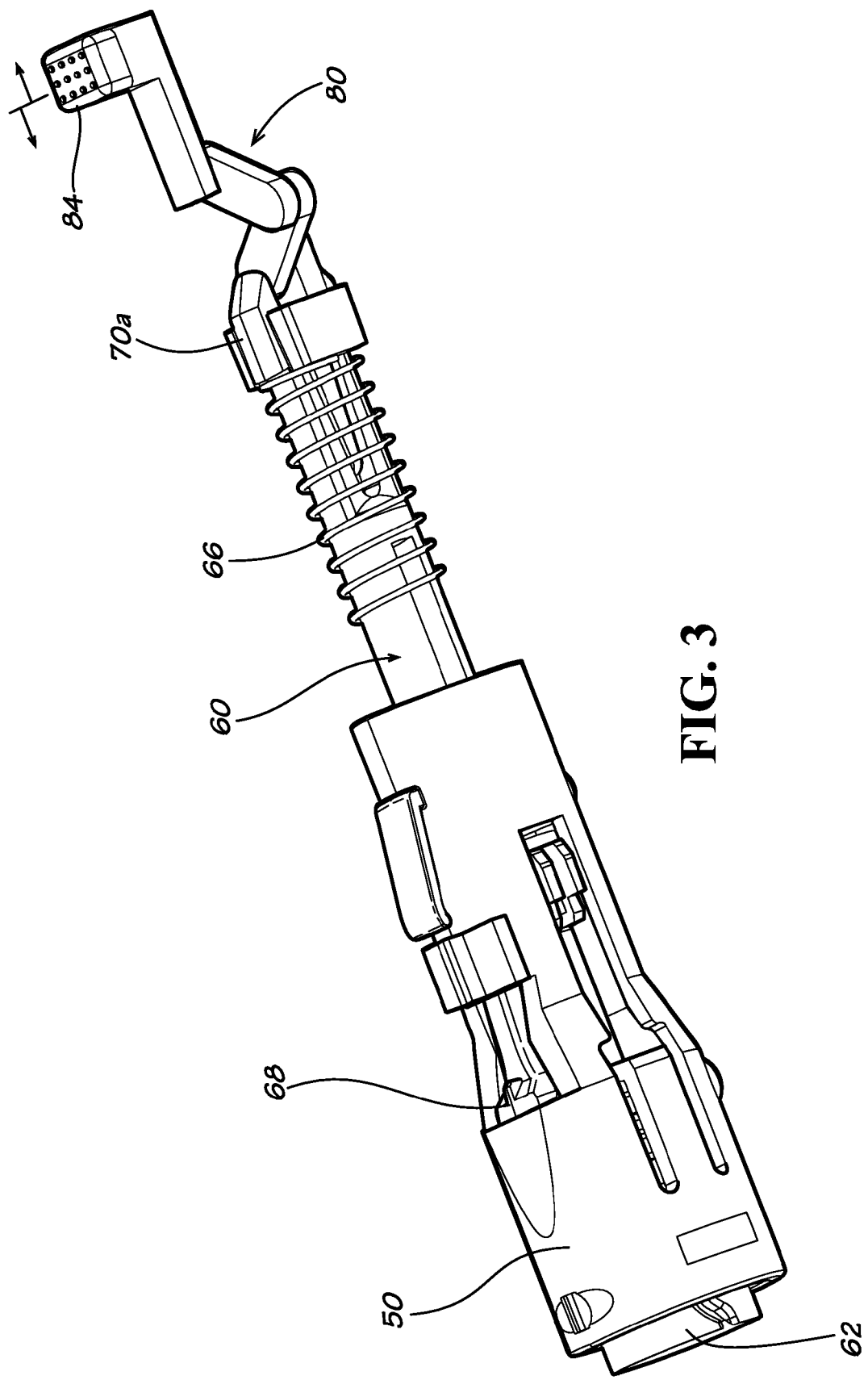
FIG. 3 is a perspective view of an inner housing core, drive mechanism and depth-control mechanism of the lancing device of FIG. 1.
Figure 4:
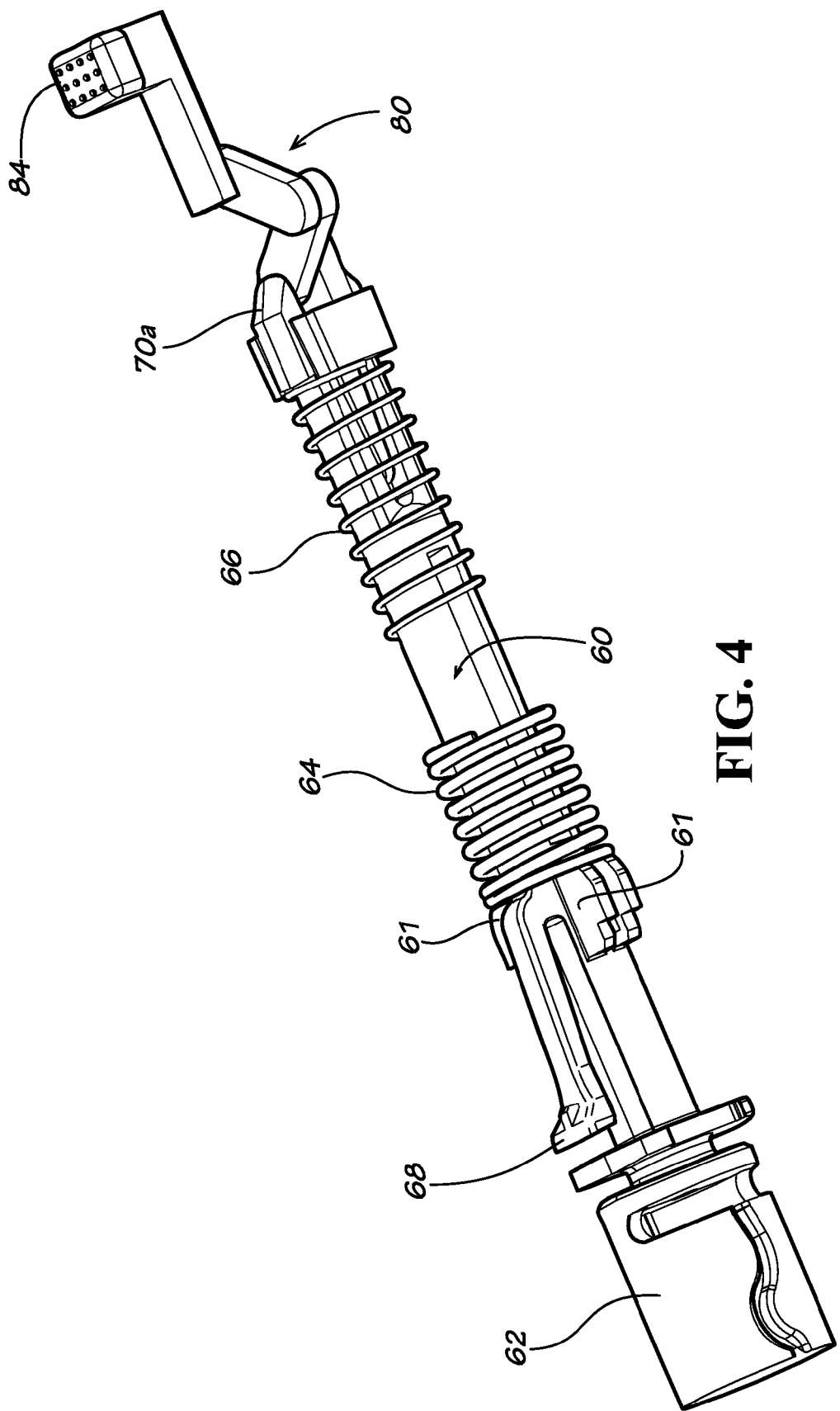
FIG. 4 is a perspective view of the drive mechanism and depth-control mechanism of the lancing device of FIG. 1.
Figure 5:
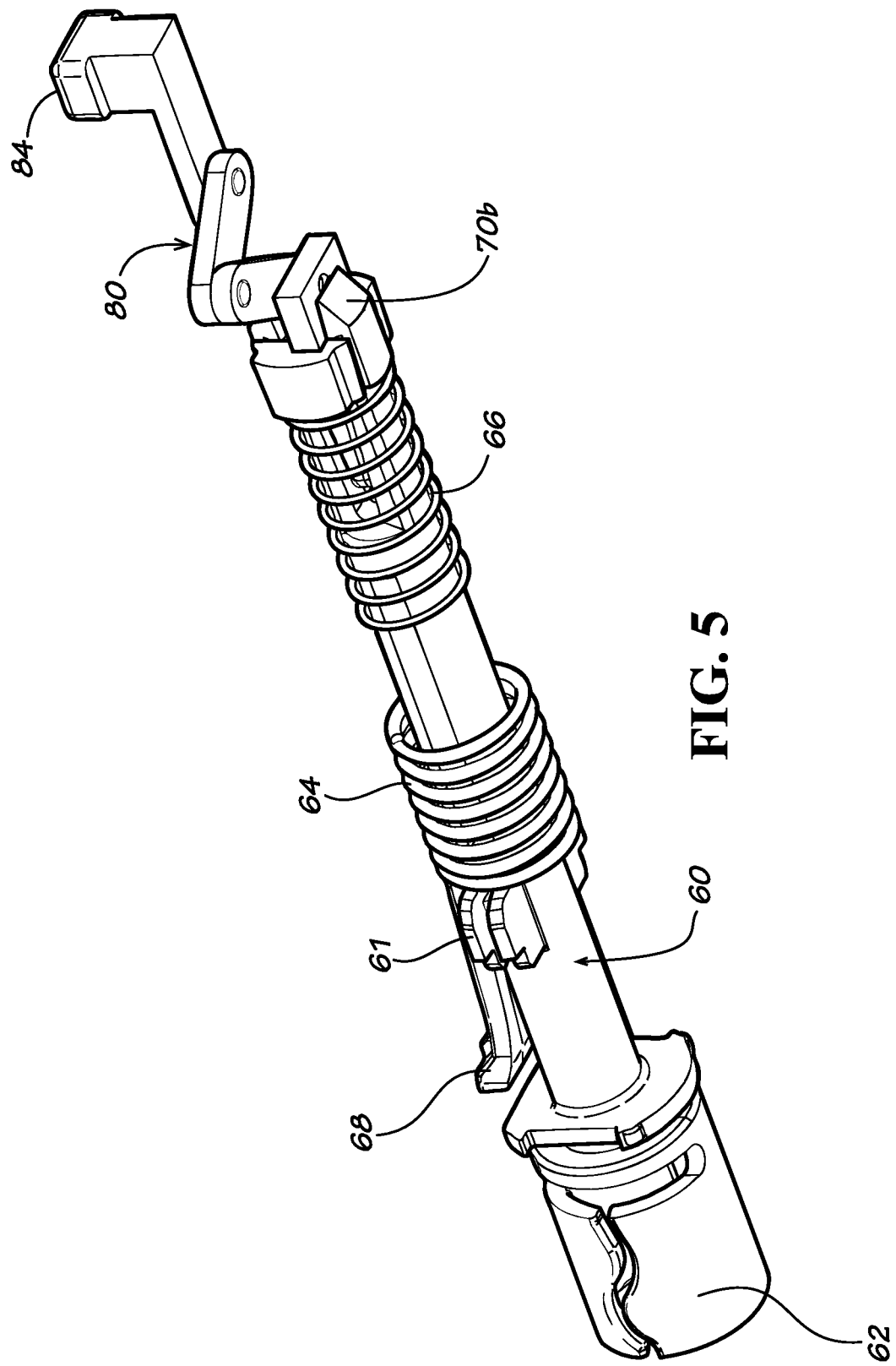
FIG. 5 is a rear perspective view of the drive mechanism and depth-control mechanism of the lancing device of FIG. 1.

FIG. 2 shows the lancing device 10 with its upper housing shell 22a and an upper portion of the charging handle 30 removed. An inner drive core 50 is engaged in a fixed position within the housing 20 by one or more interengaging surface features or couplings, and is shown in greater detail in FIG. 3. FIGS. 4 and 5 show an inner drive mechanism that is translationally mounted to slide within an axial bore or channel through the drive core 50. As depicted, the drive mechanism includes a lancet carrier 60 having a collar or sleeve 62 at a proximal end thereof for releasably engaging a lancet. A drive spring 64 is engaged between shoulders 61 on the lancet carrier 60 and the drive core for propelling the lancet carrier along the forward portion of the lancing stroke. A return spring 66 is engaged at a distal end of the lancet carrier 68 for returning the lancet carrier from its extended position to a retracted position within the housing after lancing has been completed. A cantilevered release finger 68 projects from the axial shaft of the lancet carrier 60 for releasable engagement with a catch surface (not shown) of the drive core 50 to retain the lancet carrier in its retracted position when the device is charged. The release finger 68 is contacted, and depressed/deflected, by the release button 40 being depressed to release the lancet carrier 66 to travel along its lancing stroke and thereby initiate the lancing procedure. As depicted, the distal end of the lancet carrier 60 includes a split yoke having a pair of resilient forks 70a, 70b to permit installation and retention of the return spring 66. As depicted, a linkage joint or tether 80 is secured at the distal end of the lancet carrier 60 within the resilient forks 70a, 70b, for example with a friction fit. The linkage joint or tether 80 can be constructed of a rigid material or rigid material that allows for reflexive vertical deflection. Further, the linkage joint or tether can be constructed of a flexible material.

Figure 6:
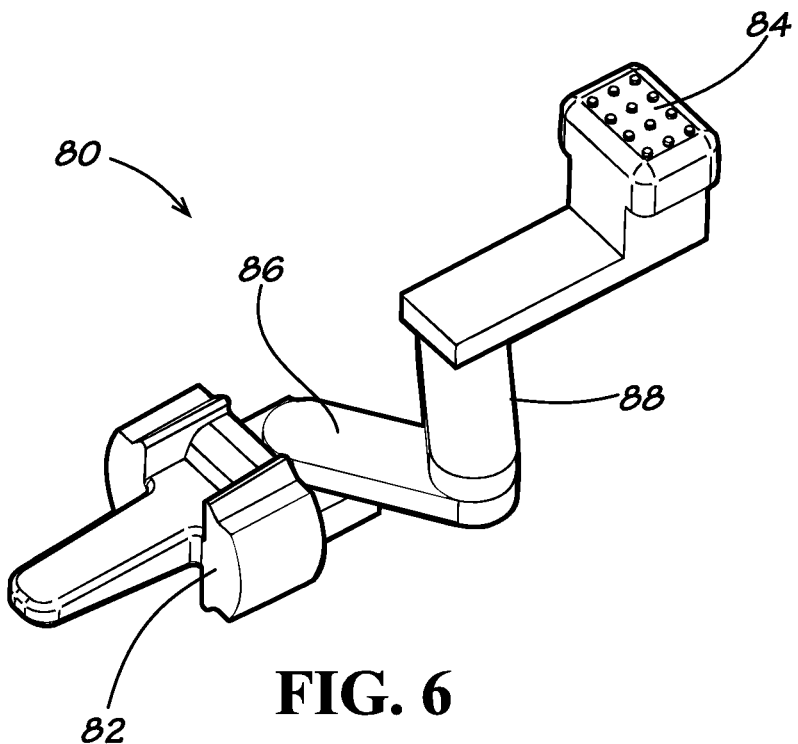
FIG. 6 is a perspective view from an upper vantage point of the depth-control mechanism of the lancing device of FIG. 1.
Figure 7:
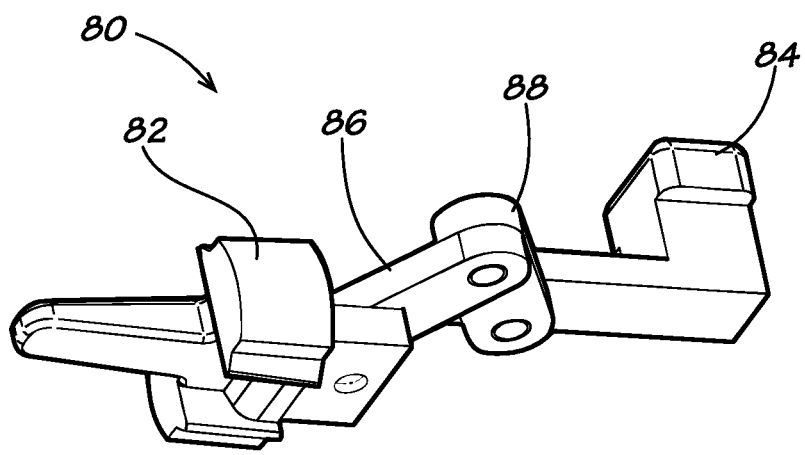
FIG. 7 is a perspective view from a lower vantage point of the depth-control mechanism of the lancing device of FIG. 1.

FIGS. 6 and 7 show details of the linkage joint or tether 80 for adjustment of the penetration or lancing depth of the lancing stroke. In the depicted embodiment, the tether 80 includes a proximal coupling 82 for attachment to the distal end of the lancet carrier 60, the distal positioning tab 84 for selective repositionable engagement with the charging handle 30, and first and second pivoting links 86, 88 connected therebetween. The first pivoting link 86 is pivotally connected at one end to the coupling 82, and is pivotally connected at the other end to the second pivoting link 88; and the second pivoting link is pivotally connected at one end to the first pivoting link and pivotally connected at the other end to the positioning tab 84. The pivoting links 86, 88 can be vertically flexible to allow the positioning tab 84 to be pushed downward during distal and proximal movement within the opening 83. One or more releasable engagement features or contacts secure the positioning tab 84 in a user-selected position in the elongated opening 83 on the charging handle 30 or other portion of the housing, to permit indexed or continuously variable positional adjustment. Example engagement features can include rigid points or a lip corresponding with cut-outs or notches in the surface of the opening 83, rubberized friction pads, or similar gripping elements.

Figure 8:
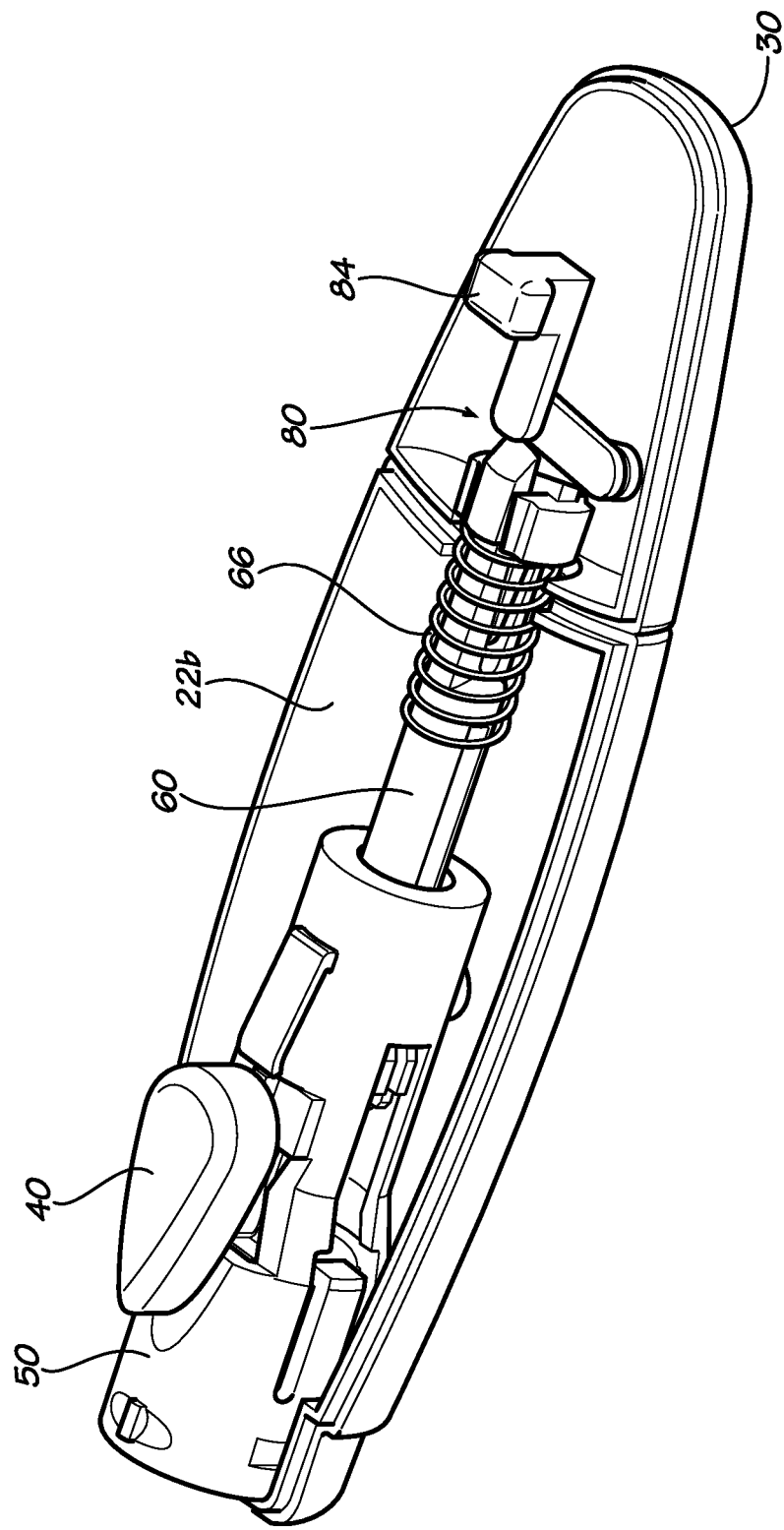
FIG. 8 is a perspective view of the lancing device of FIG. 1 with portions of its external housing removed to show internal components thereof and with the depth-control mechanism at its deepest setting.
Figure 9:
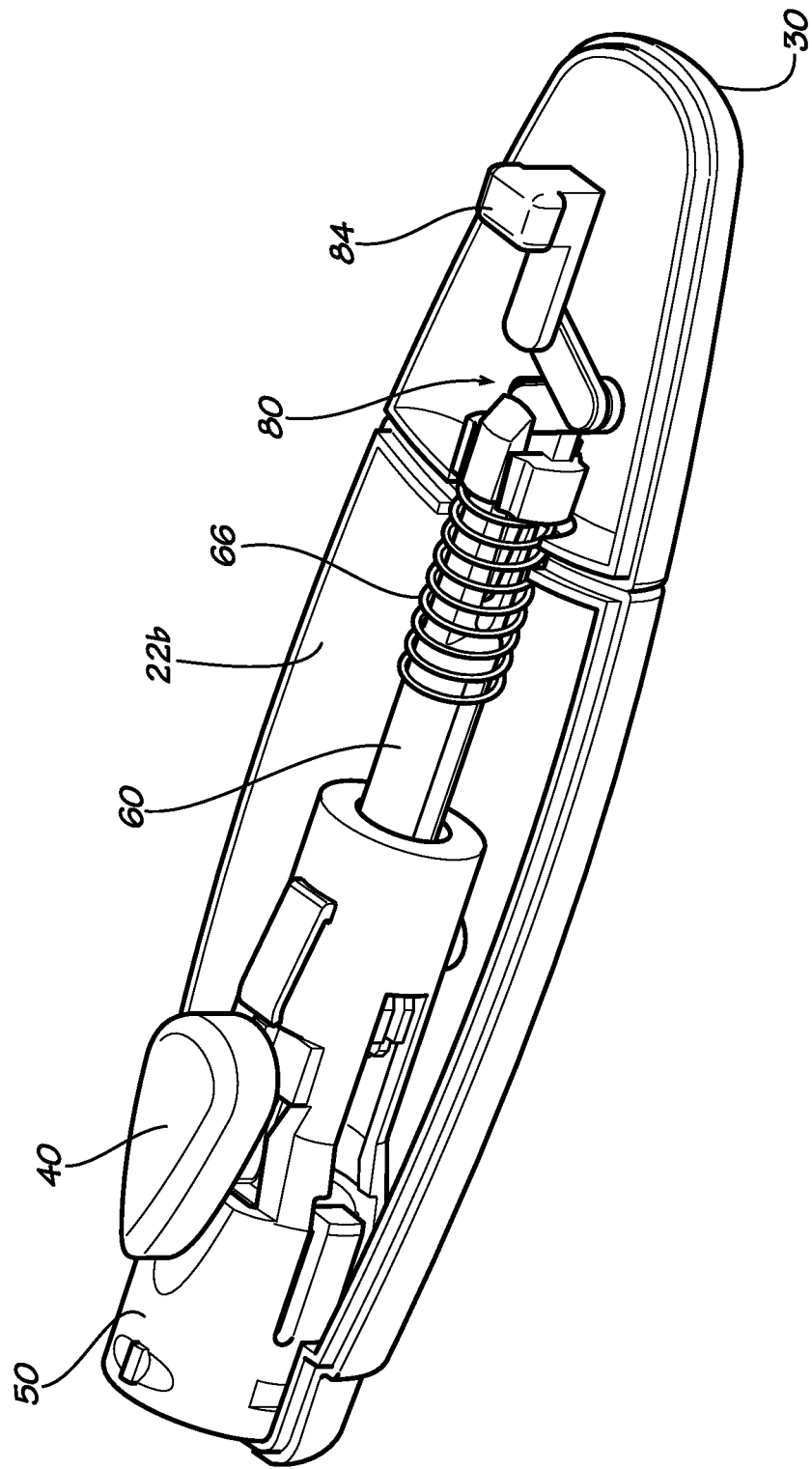
FIG. 9 is a perspective view of the lancing device of FIG. 1 with portions of its external housing removed to show internal components thereof and with the depth-control mechanism at its shallowest setting.
Figure 10:
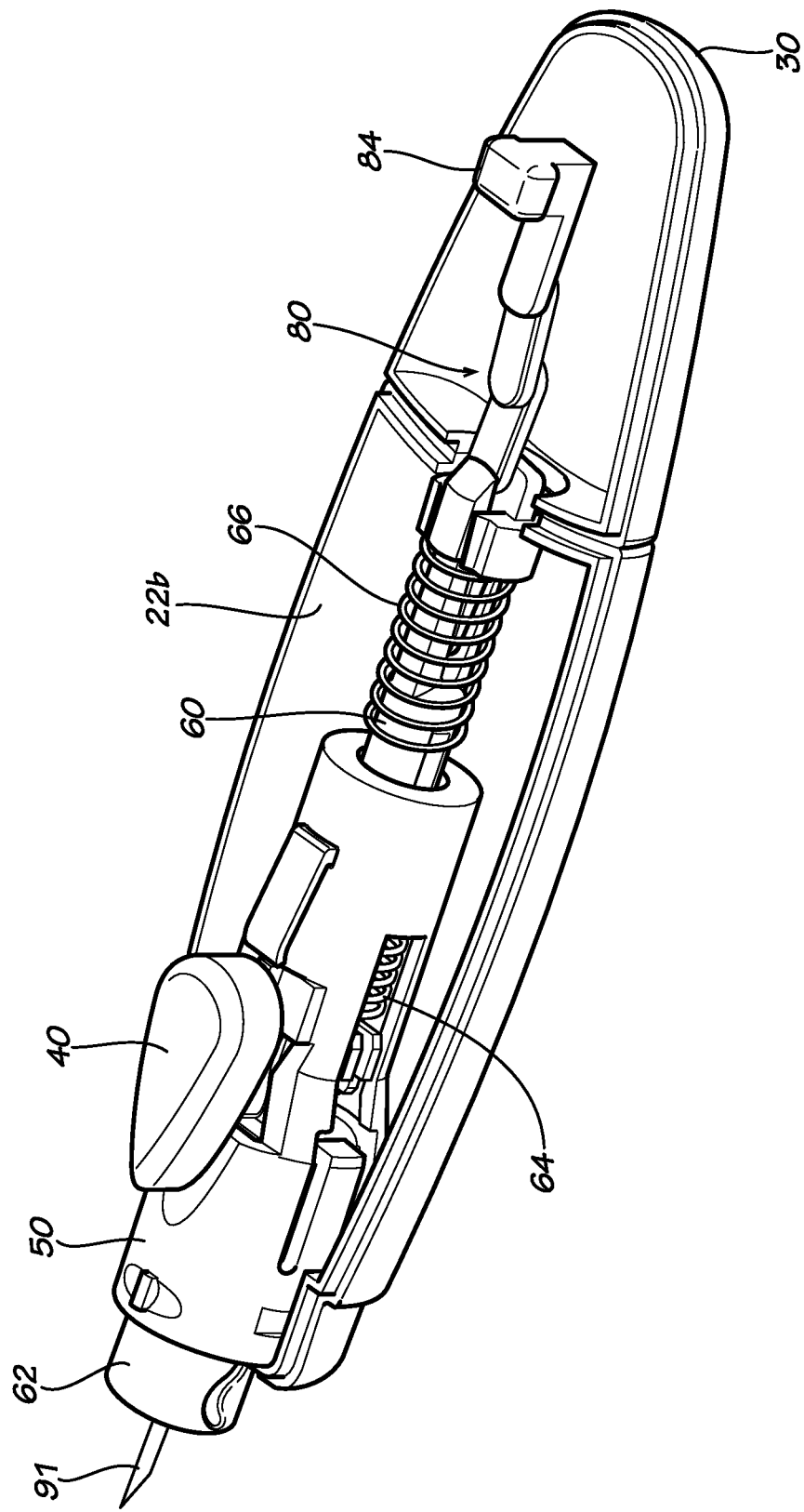
FIG. 10 is a perspective view of the lancing device of FIG. 1 with portions of its external housing removed to show internal components thereof and with the lancing device in an active and extended position.

When the lancing device 10 is actuated, the penetration depth of the lancet is limited by the extent of travel of the lancet carrier 60 in the forward or proximal direction, relative to the housing 20. The forward extent of travel of the lancet carrier 60 is, in turn, limited by the connection—provided by the linkage or tether 80—between the lancet carrier and the charging handle 30 and/or other portion of the housing. Further extension is prevented by limiting the forward motion of the lancet carrier and defining the penetration depth achieved by the lancing procedure. As the lancet carrier moves into its forward or extended position, the first and second links 86, 88 pivot from a retracted, transversely offset, and/or axially unaligned configuration (shown in FIGS. 6-9) into an extended and/or axially aligned configuration (shown in FIG. 10). As shown in FIG. 10, when actuated the lancet carrier, sleeve 62 and lancet tip 91 extend outwardly from the proximal end of the drive core 50. The housing and charging handle 30 each include cut-out sections that can align and mirror each other. As shown in FIGS. 8-10, the lancet carrier 60 rests within this cut-out section.

As depicted, the area of the cut-out is large enough for the proximal coupling 82 to travel therebetween. By selectively repositioning the positioning tab 84 in a proximal direction along the charging handle opening 83 (shown in FIG. 8), the lancing depth is increased because the distance of transverse motion that is necessary to axially align the links is greater. By contrast, selectively repositioning the positioning tab 84 in a distal direction along the charging handle opening 83 (shown in FIG. 9), the lancing depth is decreased because the distance of transverse motion that is necessary to axially align the links is less. Thus, the positioning tab 84 acts as an anchor, and repositioning it to different points longitudinally (along the axis of the lancing stroke) allows the lancet carrier to travel the same distance in the lancing stroke, but start and stop at different points. In alternate embodiments, the penetration depth is adjusted by shortening or lengthening the length of the flexible linkage or tether in its extended or axially aligned configuration, and/or by limiting the extent to which the flexible linkage or tether may extend or align to a greater or lesser extent. And, in other alternative embodiments: more than two pivoting links can be included; stop members can be provided on the links; the housing, or another device component can be provided to limit the pivoting of the links (e.g., to an extended but non-aligned configuration); and the repositioning tab can be repositionable other than longitudinally (e.g., transversely or arcuately) to adjust the lancing depth.

Figure 11:
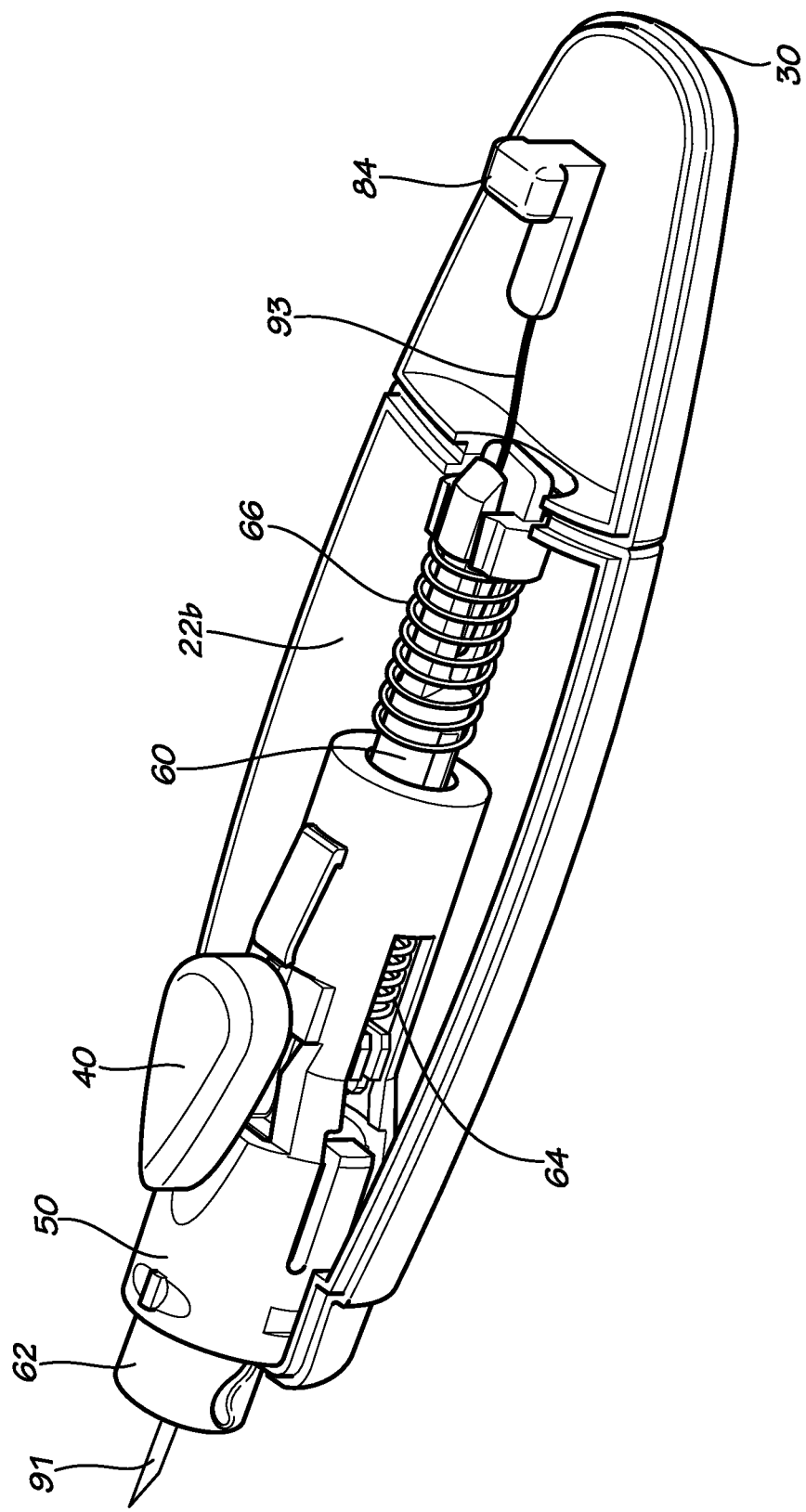
FIG. 11 is a perspective view of a lancing device of FIG. 1 showing an alternative example embodiment depth-control mechanism.

In a further alternative embodiment shown in FIG. 11, the flexible linkage or tether comprises a single link of cord, ribbon, string, wire or other flexible material 93, having a first end connected to the lancet carrier and a second end connected to the tab 84 in the housing or charging handle. The tether is flexible to permit repositioning of the positioning tab, but is not generally longitudinally flexible to ensure consistent lancing depth.

While the invention has been described with reference to preferred and example embodiments, it will be understood by those skilled in the art that a variety of modifications, additions and deletions are within the scope of the invention, as defined by the following claims.

What is claimed is:

1. A depth-control mechanism for a lancing device comprising a drive-mechanism-driven lancet carrier translatably secured within a housing, the depth-control mechanism comprising:
    an engagement body, the engagement body adapted to repositionably engage along the housing; and
    a tether adapted to be connected between the engagement body and the lancet carrier, the tether is adapted to transition between a retracted state and an extended state;
    wherein the depth-control mechanism is adapted to control the distance the lancet carrier is driven with respect to the housing by operatively advancing and retracting the engagement body translationally along the housing.

2. The depth-control mechanism of claim 1, wherein the tether comprises at least two pivotal links.

3. The depth-control mechanism of claim 1, wherein the tether comprises a first member pivotally connected with respect to the lancet carrier and a second member pivotally connected with respect to the engagement body.

4. The depth-control member of claim 3, wherein the first member is pivotally connected with respect to the second member.

5. The depth-control member of claim 4, wherein the first member and the second member are adapted to pivot horizontally with respect to the lancet carrier.

6. The depth-control member of claim 1, wherein the tether comprises a length of flexible material.

7. The depth-control mechanism of claim 1, wherein the engagement body is a positioning tab longitudinally repositionable with respect to the housing.

8. The depth-control mechanism of claim 7, wherein the tether comprises a first link adapted to be pivotally connected to the lancet carrier and a second link pivotally connected to the positioning tab, the first and second links being pivotally connected to one another.

9. The depth-control mechanism of claim 7, wherein the housing comprises a plurality of position settings for positioning the positioning tab.

10. A depth-control mechanism for a lancing device comprising a drive-mechanism-driven lancet carrier translatably secured within a housing, the depth-control mechanism comprising:
    an engagement body, the engagement body adapted to repositionably engage along the housing; and
    a joint comprising a first member pivotally connected with respect to the engagement body and a second member adapted to be pivotally connected with respect to the lancet carrier, the first member being pivotally connected to the second member;
    wherein the depth-control mechanism is adapted to control the distance the lancet carrier is driven with respect to the housing by operatively advancing and retracting the engagement body translationally along the housing.

11. The depth-control mechanism of claim 10, wherein the engagement body is a positioning tab longitudinally repositionable with respect to the housing.

12. The depth-control mechanism of claim 11, wherein the housing comprises a plurality of position settings for positioning the positioning tab.

13. A depth-control mechanism for a lancing device comprising a drive-mechanism-driven lancet carrier translatably mounted within a housing, the depth-control mechanism comprising:
    positioning tab longitudinally repositionable with respect to the housing; and
    a tether adapted to be connected between the positioning tab and the lancet carrier, wherein the tether is adapted to transition between a retracted state and an extended state; and
    wherein the depth-control mechanism is adapted to control the distance the lancet carrier is driven with respect to the housing, by operatively advancing and retracting the positioning tab translationally along the housing.

14. The depth-control mechanism of claim 13, wherein the tether comprises a plurality of pivotally connected links.

15. The depth-control mechanism of claim 13, wherein the tether comprises a length of flexible material.

16. The depth-control mechanism of claim 13, wherein the housing comprises a plurality of position settings for positioning the positioning tab.

* * * * *